United States Patent
Kostrzewa et al.

(10) Patent No.: US 11,142,784 B2
(45) Date of Patent: Oct. 12, 2021

(54) MASS SPECTROMETRIC RESISTANCE DETERMINATION BY MEASURING METABOLISM

(71) Applicant: Bruker Daltonik GmbH, Bremen (DE)

(72) Inventors: Markus Kostrzewa, Lilienthal (DE); Katrin Sparbier, Bremen (DE)

(*) Notice: Subject to any disclaimer, the term of this patent is extended or adjusted under 35 U.S.C. 154(b) by 1037 days.

(21) Appl. No.: 15/112,212

(22) PCT Filed: Jan. 14, 2015

(86) PCT No.: PCT/EP2015/050526
§ 371 (c)(1),
(2) Date: Jul. 18, 2016

(87) PCT Pub. No.: WO2015/107054
PCT Pub. Date: Jul. 23, 2015

(65) Prior Publication Data
US 2016/0333388 A1   Nov. 17, 2016

(30) Foreign Application Priority Data

Jan. 17, 2014   (DE) .................. 10 2014 000 646.8

(51) Int. Cl.
C12Q 1/18 (2006.01)
C12Q 1/04 (2006.01)
G01N 33/68 (2006.01)

(52) U.S. Cl.
CPC ............. *C12Q 1/18* (2013.01); *C12Q 1/04* (2013.01); *G01N 33/6851* (2013.01)

(58) Field of Classification Search
None
See application file for complete search history.

(56) References Cited

U.S. PATENT DOCUMENTS

| | | | | |
|---|---|---|---|---|
| 5,079,144 A * | 1/1992 | Carr | .............. | C12Q 1/04 435/288.1 |
| 5,434,056 A * | 7/1995 | Monget | .............. | C12Q 1/10 435/14 |
| 6,043,048 A * | 3/2000 | Johnston | .............. | C12Q 1/18 435/26 |
| 8,293,496 B2 * | 10/2012 | Govorun | .............. | G01N 33/6851 435/32 |
| 2005/0207981 A1* | 9/2005 | Barrios | .............. | A61K 49/0019 424/9.361 |
| 2011/0300552 A1* | 12/2011 | Demirev | .............. | C12Q 1/18 435/6.15 |
| 2012/0196309 A1 | 8/2012 | Peaper et al. | | |
| 2012/0264162 A1 | 10/2012 | Govorun et al. | | |
| 2013/0244230 A1 | 9/2013 | Luider et al. | | |
| 2014/0335556 A1* | 11/2014 | Franzen | .............. | C12Q 1/04 435/34 |

FOREIGN PATENT DOCUMENTS

| | | |
|---|---|---|
| DE | 102011012060 A1 | 8/2012 |
| FR | 2941961 A1 | 8/2010 |
| JP | 2009540319 A | 11/2009 |
| JP | 2012010623 A | 1/2012 |
| JP | 13535974 A | 9/2013 |
| JP | 2013255445 A | 12/2013 |
| WO | 2010129779 A1 | 11/2010 |
| WO | 2011154517 A1 | 12/2011 |
| WO | 2012023845 A1 | 2/2012 |
| WO | 2012113699 A1 | 8/2012 |

OTHER PUBLICATIONS

JP 2013-255445 English translation, 2013.*
JP 2012-010623 English translation, 2012.*
Amikacin, Amikacin Drug Bank Entry, Webpage, 2019.*
Sussman, Peptide transport and metabolism in bacteria, Annual Review Biochemistry, 1971, 40:397-408.*
Sompolinsky, Mechanism of High-level resistance to Chloramphenicol in different *E. coli* variants, J. Gen. Microbiology, 1968, 50, 55-66.*
Kihara, Peptides and Bacterial Growth, JBC, vol. 235, No. 5, May 1960.*
Hirsch, Amino-acid utilization in bacterial growth, vol. 53, 1953.*
Smith et al., Characterization of Bacterial Phospholipids by Electrospray Ionization Tandem Mass Spectrometry, Anal. Chem. 1995, 67, 1824-1830 (Year: 1995).*
Crespo et al., Proton Transfer Reaction Mass Spectrometry . . . , J. Microbiological Methods, 86, 8-15, Jan. 2011.
Josep Villanueva et al., "A Sequence-Specific Exopeptidase Activity Test (SSEAT) for "Functional" Biomarker Discovery" Molecular and Cellular Proteomics, vol. 7, No. 3, pp. 509-518, 2008.

* cited by examiner

*Primary Examiner* — Louise W Humphrey
*Assistant Examiner* — Srikanth Patury
(74) *Attorney, Agent, or Firm* — Benoit & Côté Inc.

(57) ABSTRACT

The invention relates to a mass spectrometric method to determine microbial resistances to antibiotics. The decrease or modification of specific nutrient components by microbes, and thus the metabolism of the microbes, is determined mass spectrometrically in culture media containing antibiotics. Hence it is not the microbes which are introduced into the mass spectrometric analysis, but the culture medium. The special nutrient components which are subject to the mass spectrometric observation are indicators for the metabolism exhibited by the microbes in the culture in the presence of antibiotics, and are thus indicators for their susceptibility or resistance.

10 Claims, 1 Drawing Sheet

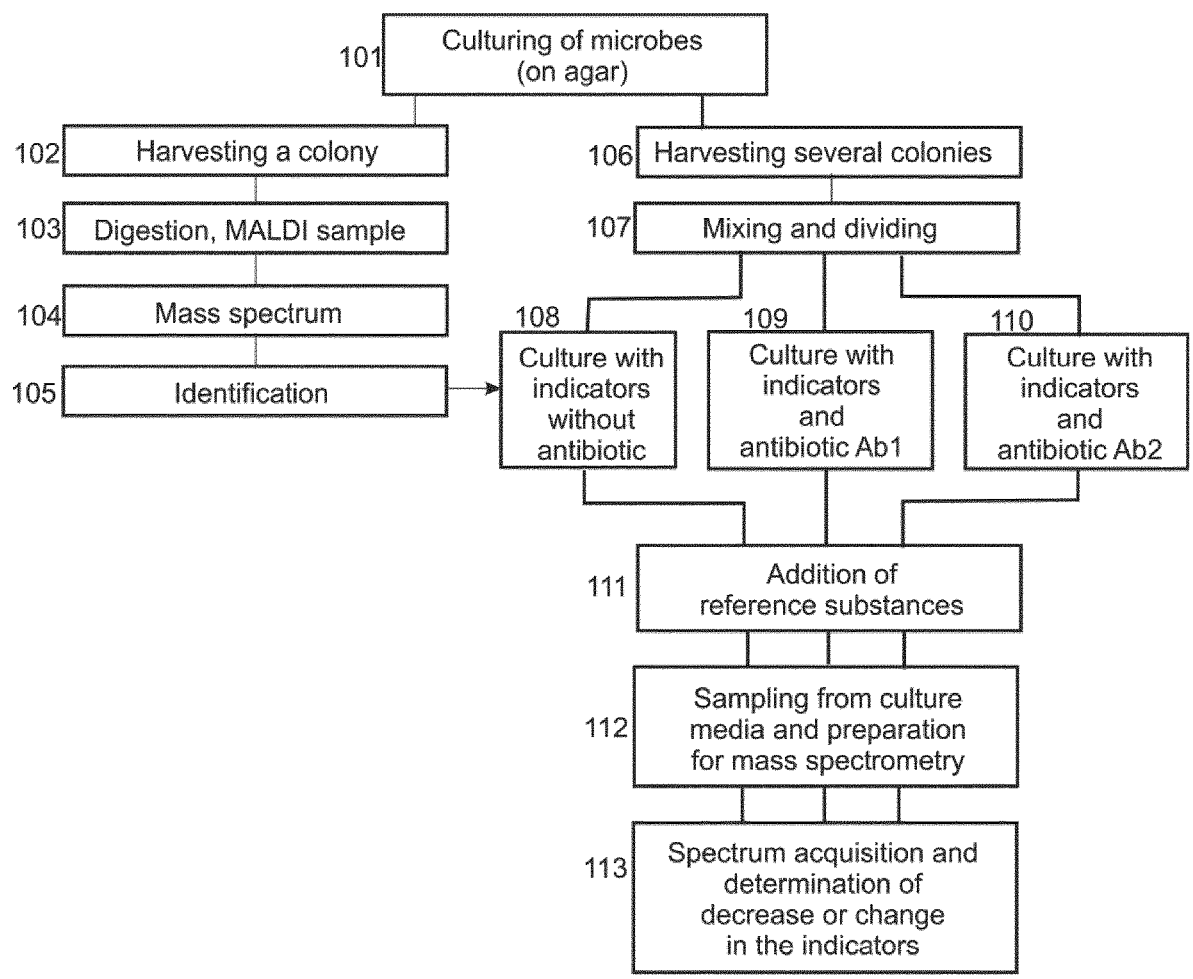

MASS SPECTROMETRIC RESISTANCE DETERMINATION BY MEASURING METABOLISM

The invention relates to a mass spectrometric method to determine microbial resistances to antibiotics.

Definitions

Instead of the statutory "unified atomic mass unit" (u), this document uses the "dalton", which was added in the last (eighth) 2006 edition of the document "The International System of Units (SI)" of the "Bureau International des Poids et Mesures" on an equal footing with the unified atomic mass unit. As is noted there, this was done primarily in order to allow the use of the units kilodalton, millidalton and similar.

For reasons of simplicity, only the term "peptides" is used in this document, although the molecules concerned could also be proteins. In the prior art, the transition from the lighter peptides to the heavier proteins is smooth and not clearly defined.

When the term microorganisms, also referred to below as germs and as microbes, is used here, it refers to microscopically small organisms which include bacteria, unicellular fungi (e.g. yeasts), microscopic algae and protozoa, for example. The singular "microorganism" or "microbe" is used for an individual microbial cell as well as a microbe strain or isolate of genetically identical microbial cells. The plural "microbes" generally means the microbial cells under analysis.

As is usual in general parlance, the term "antibiotic" means a pharmacologically active substance for the treatment of microbial infectious diseases.

PRIOR ART

Ever since penicillin was used as the first pharmacological antibiotic, microbial strains have increasingly developed various types of resistance to different types of antibiotics, or acquired them from other microbes, i.e. the microbes acquired characteristics which allow them to weaken the effect of antibiotic substances or neutralize it completely. Meanwhile, unfortunately, resistances are frequent; microbes occurring in hospitals are predominantly resistant nowadays. In some cases it is possible to predict the resistance of a microbe transmitted within a hospital to antibiotics usually used in the hospital; this does not, however, apply to infections which were contracted outside the hospital. Commercially used methods of determining resistances which detect the bacterial growth zone on nutrient media containing antibiotics, or the growth-related change in opacity in liquid cultures containing antibiotics, are time-consuming, and usually take more than one working day; a fast determination of the antibiotic resistance of a microbial sample or a microbial isolate is extremely important, however. Rapid spectrometric methods are being developed.

The patent specification DE 10 2006 021 493 B4 (V. M. Govorun and J. Franzen, 2006, corresponding to GB 2438066 B, U.S. Pat. No. 8,293,496 B2; called "Govorun" in the following) discloses mass spectrometric methods for determining the resistance of microbes, in which protein profiles of the microbes are measured mass spectrometrically after being cultured in media with and without added antibiotics, and compared.

Specifically to detect resistance to beta-lactamases (penicillins and related substances), mass spectrometric methods have been developed which are disclosed in the documents DE 10 2010 023 452 B4 (M. Kostrzewa et. al) and DE 10 2011 012 060 A1. They are based on measurement of the breakdown of specific substrates, which are similar to the antibiotics, in the vicinity of the microbes.

In the application documents EP 13002450.8 (K. Sparbier et al) and EP 13002699.0 (K. Sparbier and C. Lange), further mass spectrometric methods to determine resistances are described, whereby the uptake of isotopically labeled nutrient components, or the increase in the microbial biomass in the presence of antibiotics, is measured: The uptake of isotopically labeled nutrients or the increase in biomass indicates resistance. These methods are not limited to specific types of resistance, and therefore do not only indicate resistance to beta-lactamases. These two application documents are therefore to be included here by way of reference. They also contain introductions to the problem of resistances in general and of mass spectrometric determination of resistances in particular, and the importance of fast resistance determinations is explained.

It has so far been found that the methods of these two application documents each produce optimal results for different microbe species and different antibiotics; as is so often the case, no universally applicable methods are (yet) available here either. There is therefore a definite need for further methods for determining resistances.

Objective of the Invention

The objective of the invention is to provide a mass spectrometric method and suitable synthetic culture media with which the resistance of microbes to one or more antibiotics can be determined with certainty, at low cost and, most importantly, quickly. The resistance determination for fast-growing, and thus especially dangerous, pathogens should take less than one hour, if possible.

BRIEF DESCRIPTION OF THE INVENTION

The invention provides a method for the mass spectrometric determination of microbial resistances to an antibiotic, whereby the microbes are grown in a culture medium which contains a specific concentration of the antibiotic. The method is characterized by the fact that it involves a mass spectrometric determination of whether at least one nutrient component of the culture medium decreases during culture or a chemically modified variant of a nutrient component newly appears and increases. A decrease in a nutrient component or an increase in a chemically modified variant of a nutrient component indicates resistance to the antibiotic at this particular concentration. Chemically modified variants can be produced by methylation, acylation, acetylation, oxidation or similar reactions, but particularly by the breakdown of a nutrient component. The appearance of a new substance and its increase is usually easier to measure than the decrease in an already present nutrient component.

The preferred nutrient components are peptides, whose decrease or chemical modification is determined. In particular, peptides which have a core of D-amino acids are used, with the formation and increase in peptides comprising only this core being measured mass spectrometrically. It is also possible to use peptides consisting of isotopically labeled amino acids, where the formation of isotopically labeled peptides of shortened length in the culture medium is measured mass spectrometrically. The decrease in a nutrient component, or the increase in a chemically modified variant, can be determined with the aid of a reference substance added in a measured amount. The measurement of a chemically modified variant often does not require a reference substance, however, or can be done in comparison to the unmodified nutrient component. One or more reference substances can be added in measured amounts after the culture is finished. The reference substances are preferably peptides made up of D-amino acids.

In one embodiment, the microbes undergo a pre-culture in a first culture medium containing antibiotics, before the pre-cultured microbes are grown further in a second culture medium. The decomposition of a nutrient component or the increase in a chemically modified variant of a nutrient component of the second culture medium is then measured mass spectrometrically.

In a further embodiment, the microbes undergo a pre-culture with the antibiotic before a further nutrient component is added. The decomposition of this nutrient component, or the increase in a chemically modified variant of this nutrient component, is measured mass spectrometrically. The further nutrient component is preferably a peptide, whose addition is closely followed by the addition of inhibitors for secreted peptidases to the culture medium.

The microbes under analysis can be divided up, the portions being grown simultaneously in a first culture medium without antibiotics and in a second culture medium containing an antibiotic. It is preferable if the microbes under analysis are grown in several culture media with the antibiotic at different concentrations in order to determine the strength of resistance. The microbes can also be divided up into a higher number of portions, which are then grown simultaneously in corresponding number of culture media, one without any antibiotic, the others with different types of antibiotic at different concentrations in each case.

The invention also provides a synthetic culture medium which contains suitable nutrient components for the method according to the invention, particularly peptides which contain a core of D-amino acids.

The invention thus provides methods which, in contrast to the two application documents referenced above, are not based on Govorun's method; the objective of the invention is rather to determine the decrease in special nutrient components, or the increase in chemically modified variants of specific nutrient components, in the environment around the microbes in the presence of antibiotics in microbe cultures, for example by enzymatic decomposition, and thus to determine the metabolism of surviving microbes by mass spectrometry. It is therefore not the microbes that undergo mass spectrometric analysis, but components of the culture media. The special nutrient components and the modification products which are observed by mass spectrometry are called "indicators" here. They are indicators for the intact or impaired metabolism of microbes in the culture when antibiotics are present.

Microbes take up nutrient components from their environment, partly to produce energy, partly to synthesize substances which are used for the internal structure of the microbes. Proteins, fats and especially carbohydrates serve as nutrient components for the microbes. Smaller molecules can be taken up directly through the cell wall with the aid of various mechanisms; more complicated methods are available for larger molecules, including external digestion by secreted enzymes. When the metabolism is intact, nutrient components can also be modified by oxidation, acylation, methylation, or acetylation.

As long as the microbes still have an intact metabolism in the culture medium in the presence of antibiotics, at least some nutrient components in a culture will decrease or appear in a modified form; suitably chosen nutrient components in appropriately constituted culture media can thus be observed mass spectrometrically as indicators of a normal or abnormal microbial metabolism. When the antibiotics have caused the metabolic function, and hence the vital functions, to cease, the decrease in, or modification of, the indicators essentially stops, at least if enzymes secreted earlier do not continue to act as a catalyst. Measures can be taken against enzymes secreted earlier. If the indicators do not then continue to decrease in the presence of an antibiotic, and if modified forms no longer increase, this indicates that the microbes are susceptible to this antibiotic. The invention is based on the mass spectrometric measurement of the decrease in these indicators or the appearance of modified forms of the indicators in the culture medium.

An indicator should ionize well, be clearly recognizable in mass spectra, be preferably taken up by microbes as nutrient, and not be present in too large a quantity, so that its decrease can be followed quantitatively. It should also be possible to detect the chemically modified forms of the indicators easily. The take-up or modification of the indicators must not be limited by surplus nutrient which is easier to take up. If a peptide is used as an indicator, for example, the culture medium should not contain amino acid components which are easier to take up.

The detectability of the indicator can be enhanced by isotopic labeling, especially if a mass spectrometer with the possibility of fragment ion analysis is used. If an isotopically labeled indicator is used, an exo-enzymatic cleavage of the indicator can also be observed particularly well by mass spectrometry. It is also possible to synthesize indicators which provide predetermined degradation products which cannot be broken down further and serve as special indicators in the mass spectrum.

In order to quantify the decrease in the indicators, suitable reference substances are added in precise quantities. Substances which cannot as such be broken down or taken up by the microbes can be used as reference substances. For example, peptides which are similar to the indicators, but longer or shorter than the indicators by one amino acid, and which consist only of D-amino acids instead of the natural L-amino acids, can be used as reference substances. This means that they cannot be attacked by the natural peptidases. The reference substances can also preferably be added only after the culture is finished in order to avoid any digestion. The reference substances can also be labeled with isotopes. A decrease in the indicators compared to the reference substances on the expected scale, or the appearance of chemically modified variants of the indicators, shows that the microbes under analysis are resistant to the antibiotics at the concentration used; susceptible microbes exhibit no decrease in the indicators when the concentration of the antibiotic is above the minimum inhibitory concentration (MIC).

The optimal nutrient components for use as indicators depend on the microbe species, but the species is usually known, since the determination of resistance is generally preceded by an identification of the microbe species.

Matrix-assisted laser desorption (MALDI) and related methods, and also electrospray ionization (ESI), or other types of ionization can also be used as ionization methods. For MALDI, components of the culture media are dried, together with matrix substances, on a suitable sample support during the preparation. With ESI, the culture media are sprayed in the liquid state. All mass spectrometers which are equipped with ion sources for these types of ionization can be used.

In order to at least roughly estimate the strength of resistance, cultures with an added antibiotic at various concentrations can be used. To test the resistance to several antibiotics, it is possible to simultaneously prepare several cultures with several antibiotics, also with mixtures of several antibiotics, and where necessary, even with different concentrations of the antibiotics in each case.

Ready-made culture media with suitable indicators and different antibiotics, and solutions with reference substances can also be provided. In the case of commercially available sample supports with sample sites for MALDI ionization, which have pre-prepared thin layers of the matrix substance, these thin layers can already contain reference substances in measured quantities.

BRIEF DESCRIPTION OF THE FIGURE

FIG. 1 shows an example of a flow diagram for a method of identifying a microbe and determining its resistance to (here) two antibiotics AB1 and AB2 according to this invention.

PREFERRED EXAMPLE EMBODIMENTS

As has already been mentioned above, the invention provides methods which are not based on Govorun's method, unlike the last two application documents referenced above. The objective of the invention is rather to determine the decrease in special nutrient components, or the appearance of, and increase in, chemically modified variants (for example by enzymatic reactions) of special nutrient components, called "indicators" here, in the microbe culture, when antibiotics are present. This enables the metabolism of the surviving microbes to be determined by mass spectrometry. Thus it is not the microbes or their components that are introduced to the mass spectrometric analysis, but preferably only components of the culture medium, for example after the microbes have settled in the liquid through gravitation or after they have been removed by centrifugation or filtration.

Microbes can take up nutrient components from their surroundings in different ways. The nutrient components serve partly to produce energy, and partly to build the internal structure of the microbes through the synthesis of substances. Proteins, fats and carbohydrates can serve as nutrient components of the microbes. The take-up of the nutrient components follows different, sometimes quite complex routes, including the chemical modification or enzymatic cleavage of the nutrient components, often outside the microbial cell.

The cell walls of archaea, yeasts, Gram-positive and Gram-negative bacteria have a very different structure, but usually have a hard-elastic wall structure (for bacteria, this structure comprises peptidoglycans, a relatively porous network of polysaccharides and tetrapeptides). In addition, they have membranes, both outside and inside, with embedded proteins (for example porins), which serve many purposes, primarily the transport of molecules through the cell wall, especially the cell membranes. The cell walls of the microbes are naturally permeable only to gases and very small, neutral molecules measuring up to a few hundred daltons. For ions and most biologically active substances, they are an insurmountable barrier unless assistance is provided. All vital processes and specific cell functions are, however, dependent on the cell participating in a selective exchange of substances or particles with its environment. Therefore, extremely selective mechanisms exist which allow molecules to pass through the cell wall, e.g. channels or so-called carriers.

For eukaryotic microorganisms, endocytosis is a special transport process for large molecules through to smaller particles. Endocytosis is the term used for an invagination process of the cell wall, whereby an individual cell or a compartment engulfs a drop of liquid, with certain substances dissolved therein: macromolecules or larger nutrient particles through to other smaller cells. At the end of the invagination process, a so-called endosome is pinched off or pushed off into the cell's interior and is now part of the endomembrane system. The cell thus incorporates a portion of the surrounding medium into its interior. Also important is receptor-mediated (or receptor-controlled) endocytosis, whereby special receptors on the cell surface are responsible for identifying the particle to be incorporated. Endocytosis is the opposite of exocytosis, whereby substances such as metabolites which are no longer required are released to the outside. Endocytosis and exocytosis are normally in equilibrium, if only to keep the area of the cell wall the same in terms of size.

With bacteria in particular, but also with yeasts, larger molecules can also be broken down externally by excreted enzymes ("exoenzymes") or modified by oxidation, acylation, acetylation, or methylation in order to allow them to be transported through the cell wall. The molecules which are created from these modifications are also suitable as indicators of an intact or impaired metabolism.

Regardless of how exactly the nutrients are taken up, the nutrient take-up reduces the concentration of some nutrient components in the nutrient medium of a culture if the microbes are viable in the culture medium and have an intact metabolism; these nutrient components can be mass spectrometrically observed as indicators that the microbes have a normal or abnormal metabolism. If the decrease is based on a chemical modification (for example enzymatic), then breakdown or modification products also appear and can also be observed mass spectrometrically. When the antibiotics cause the metabolic functions, and hence the vital functions, to cease, the transport of the indicators into the microbial cells stops. The degradation of the indicators and the formation of breakdown products also stops, unless these processes are continued catalytically by enzymes which have been secreted earlier. Thus, if the nutrient components do not decrease further after a short interval in the presence of an antibiotic, or if the breakdown and modification products no longer increase, this indicates that the microbes are susceptible to this antibiotic. The invention is based on the mass spectrometric measurement of the decrease in, or modification of, these indicators in the nutrient medium.

As has already been indicated, the resistance can also be determined by observing mass spectrometrically the enzymatic cleavage of the indicator, because breakdown products are then produced which were not previously present in the culture medium. If the indicator is isotopically labeled, then isotopically labeled fragments of the indicator can be found. In particular, the indicator can have a special structure which delivers an easily identifiable breakdown product. For example, a peptide serving as an indicator can have a structure whereby the central part has a core of around six to ten D-amino acids, continued at least at one end by several L-amino acids. Since the secreted proteases can only degrade L-amino acids, the core containing the D-amino acids remains undigested. This core peptide then appears (increasing over time) as a new, not previously detected substance in the mass spectrum. Many different peptides may serve as indicators, all having the same core of D-amino acids, providing at their ends the various L-amino acids required by the microbes. The core of D-amino acids can then be mass spectrometrically detected and its increase measured. It is not important here whether the peptides are broken down outside the cell, or whether the breakdown takes place within the microbial cell and the indigestible breakdown product is excreted again.

The culturing of bacteria for methods according to this invention is best undertaken in fully synthetic nutrient media, which have very clean mass spectra without much chemical background noise. Synthetic nutrient media usually contain around ten grams of glucose in one liter of water as the source of energy and the starting material for syntheses. In principle, bacteria can themselves synthesize the endogenous proteins and peptides from the digest of glucose; to this end around 0.5 g $K_2HPO_4$ have to be added as the potassium and phosphate source, around 1 g $NH_4Cl$ as the nitrogen source for amino acids, 0.2 g $MgSO_4$ as the sulfur and magnesium source for enzymes, and several trace elements. This synthesis process consumes a large amount of energy, however; the microbes avoid it if amino acids, digestible peptides or proteins, or other digestible nutrients are already present in the nutrient medium. If, for example, only a few peptides are present, but otherwise no individual amino acids, then the peptides can serve as indicators. Peptides comprising around eight to twelve amino acids are particularly favorable; this corresponds to a mass of around 1000 to 1400 daltons. For example, two peptides, each with ten amino acids, can serve as indicators, with the peptides being selected in such a way that they contain all 20 amino acids. Or three or more peptides can be used which cover all amino acids in a ratio which predominates in microbes. One of the peptides can serve as the indicator, but it is also possible to use several peptides simultaneously as indicators, since they can all be detected simultaneously in the mass spectrum of the culture medium.

For high mass spectrometric sensitivity, it is also possible to use phospholipids, although these do not contain any amino acids. It is also possible to add peptides which are derivatized in such a way that they can be ionized particularly well and thus have a high level of sensitivity for mass spectrometric identification.

Furthermore, many bacteria require a vitamin mixture of biotin (vitamin H; mass m=244 Da), nicotinic acid (vitamin B7; m=123 Da), thiamine (vitamin B1; m=335 Da), para-aminobenzoic acid (m=137 Da), pantothenic acid (vitamin B5; m=219 Da), pyridoxamine (vitamin B6; m=168 Da) and cyanocobalamin (vitamin B12; m=1355 Da). These vitamins can also be used as indicators.

The best possible nutrient components to be used as indicators can depend on the microbe species, but the species is usually known, since the determination of resistance is generally preceded by an identification of the microbe species.

The compounds added as indicators should be present in low concentration so that their decrease is easily detectable even with small quantities of microbes, which produce only a small turnover. For the same reason, the microbes, which are generally present as colonies on agar because they are cultured in this form for the identification, are added to as small a volume as possible of a liquid culture medium, amounting to only a few microliters. These volumes must, however, be accurately measured for the addition of reference substances. It is also possible to collect several colonies of the same microbe species and add them to the culture volume.

In order to quantify the decrease in the indicators, suitable reference substances are added in precisely measured quantities. Substances which in themselves cannot be broken down or taken up by the microbes, for example because of protective groups, can be used as reference substances. Particularly suitable are peptides that consist only of D-amino acids. Since it is almost impossible to prevent the microbes taking up these substances despite their indigestibility, it is advantageous to add the reference substances only after the culture has ended, in order to avoid any decrease in the concentration of these reference substances in the culture medium. A decrease in the indicators or an increase in the degradation products on the scale expected, measured with respect to the reference substances, indicates that the microbes analyzed are resistant to the antibiotic at the concentration used; susceptible microbes exhibit no decrease in the indicators if the concentration of the antibiotic is above the minimum inhibitory concentration (MIC). As indicated in the flow diagram of FIG. 1, it is expedient here to also prepare a culture without any antibiotic in order to measure the natural decrease or change in the indicators brought about by the microbes, for comparative purposes.

Mention has already been made of the fact that there is a transition period. Bacteria in a medium containing an antibiotic do not immediately stop all metabolism, even if the concentration of the antibiotic is far above the maximum inhibitory concentration. They usually have to first take up the antibiotic or allow it to take effect in other ways. In order to avoid degradation or modification of the indicators in this phase, a pre-culture with the antibiotic can be carried out and the indicator added only afterwards. The most favorable duration for this pre-culture must be determined experimentally.

It is also possible, however, that, depending on the composition of the nutrient medium, proteases have already been excreted in this pre-culture and now catalytically break down the indicator after it has been added, thus giving the impression of an intact metabolism (at least temporarily). In this case it is helpful to rinse the microbes with antibiotics after the pre-culture and put them into a fresh culture medium with indicator and antibiotic. The rinsing can take place in the known way by careful centrifugation or filtration.

It is also possible to add an inhibitor for the secreted proteases after the pre-culture in order to render them ineffective. The quantity of inhibitor must be measured in such a way that it does not also stop the proteases which continue to be secreted by the living microbes. It is also possible to subsequently neutralize any excess of inhibitor by means of a substance which in turn inhibits the inhibitor.

Both the indicators and the reference substances should be easy to ionize and provide easily recognizable peaks in the mass spectra. It has already been indicated that phospholipids have a particularly good mass spectrometric sensitivity. It is also possible to cover a larger concentration range by means of the reference substances. For example, three reference substances in ratios of 100:10:1 or 25:5:1 can be used. This can be advantageous particularly for measurements of the breakdown products, whose concentration increases from zero upwards.

All methods which ionize larger organic molecules can be used as the ionization method, especially matrix-assisted laser desorption (MALDI) and related methods, as well as electrospray ionization (ESI). For MALDI, a small volume of the culture media is dried, together with matrix substances, on a suitable sample support during the preparation. For ESI, the culture media are sprayed in the liquid state, for example by so-called nano-ESI from a small capillary tip. All mass spectrometers which are equipped with ion sources for these types of ionization can be used.

There are intermediate stages between full resistance of the microbes and full susceptibility; growth is impaired but not completely inhibited. In order to estimate the strength of resistance of microbes, the actual inhibitory concentrations of the antibiotics can be measured. The MIC values of the antibiotics (minimum inhibitory concentrations for fully susceptible microbes after many hours of exposure) are known to a large extent; but the actual inhibitory concentrations can deviate from this because it is not possible to wait for the antibiotic action to reach equilibrium, which takes hours; moreover, the MIC values increase with the strength of resistance. To measure the actual inhibitory concentrations, cultures with an added antibiotic at various concentrations can be used, which can correspond to the concentration 1×MIC, 10×MIC and 100×MIC of the known MIC values, for example. Experience shows that, with the method described, the inhibition of microbe growth at a concentration of 1×MIC is only observed if the microbes are fully susceptible. If they have weak resistance, they are only inhibited from a concentration of 10×MIC upwards, while in the case of a very strong resistance, growth is still seen even at a concentration of 100×MIC. The effect can be seen from the values of the decrease or change in the indicators. This means that for intermediate resistances, growth is different for different concentrations of the antibiotic.

If the method is carried out without graduated concentrations, a concentration of 10×MIC has been found to be particularly suitable.

To determine the resistances, it is advantageous to have ready-made synthetic culture media with favorably selected indicators available. Different types of antibiotic can already have been added to them. Ready-made solutions with reference substances can also be provided. In the case of commercially available sample supports with sample sites for MALDI ionization, which carry pre-prepared thin layers of the matrix substance, the thin layers can already contain measured quantities of reference substances. A measured quantity of the nutrient medium must then be applied. Matrix substances in pre-prepared quantities, which are commercially available in small bottles, may also already contain the reference substances.

The method is surprisingly fast. Microbes usually require a lag-time of around 20 minutes to adjust to the culture medium, after which a significant decrease in the indicators or increase in the breakdown products can be observed after a further 20 minutes if the microbes are resistant. Dangerous infections are usually caused by rapidly growing microbes with a doubling time of only about 20 minutes.

To test the resistance to several antibiotics, it is possible to prepare several cultures with several antibiotics, where necessary even with different concentrations of each antibiotic. The additional time needed to prepare and measure the samples from several cultures is of almost no consequence compared to the culture time itself.

For a quick test for multi-resistant germs (example: MRSA, methicillin-resistant *Staphylococcus aureus*), the media can also be provided with a mixture of several types of antibiotic. If the microbes grow in this mixture, they are multi-resistant.

Ionization of the dried components of the culture medium by matrix-assisted laser desorption (MALDI) requires either a sample support plate on which the matrix substance is already prepared in a thin layer, or the production of a matrix solution. Commercially available matrix substances often have the disadvantage that they are difficult to dissolve without ultrasound. Consequently, small bottles of purified and freeze-dried matrix substances in precisely measured quantities are now on the market. With these, the matrix substance dissolves immediately when the solvent is added, and the solution is immediately ready to use in the correct concentration. As defined in this invention, a carefully measured quantity of at least one reference substance can be added to the matrix substances of these products for the purpose of quantifying the breakdown or change in the indicators. In the device used for preparing the MALDI samples, the matrix solution can be applied to the dried components of the nutrient medium in a carefully measured quantity and without coming into contact with them. The sample support plates with thin matrix layers which are already sold commercially as products can also contain reference substances in measured amounts. The thin layers are each applied to small sample areas, which are well spaced and each have a diameter of around two millimeters.

One typical example for the sequence of a method to determine resistances is shown in the diagram of FIG. 1. The method is shown here with the microbes being cultured on an agar (101). The microbes of a colony are harvested (102), digested and processed into a MALDI sample (103). The acquisition of a mass spectrum (104) leads to the identification of the microbe by comparing its mass spectrum with reference spectra (105). In a routine laboratory, it takes only between 10 and 30 minutes from harvesting a colony through to the identification, depending on the number of microbe samples to be identified in parallel. In order to determine the resistance, several further colonies of the same microbes can be harvested at the same time (106). These are mixed in a culture medium and divided up for the different types of culture (107). In the example shown in this diagram, three cultures are prepared: a culture in a medium with no antibiotic (108), and two cultures with the antibiotics Ab1 (109) and Ab2 (110). In this example, the culture media already contain the indicators. It goes without saying that further cultures with further antibiotics and, if the strength of resistance is also to be determined, cultures with different concentrations of the antibiotics can be prepared. All the cultures are already prepared at the optimum temperature so that the microbes do not suffer a shock and the heating does not cause a time delay. The duration of the culture depends on the lag-time and the doubling time (generation period) of the microbes, which is known from the identification of the microbes. The culture only needs to last one to three doubling times. Around 20 to 40 minutes are sufficient for fast-growing microbes.

Media samples from the various cultures are then processed into MALDI samples after the reference substances have been added, and mass spectra are acquired (111). The mass spectrum of the medium (108) for the microbes which were cultured without any antibiotic is used to determine the normal decrease in the indicators or the increase in the breakdown products, which essentially depends on the unknown number of inoculated microbes. From the media of cultures (109) and (110), mass spectra (113) are acquired after addition of the reference substances (111) and preparation of the MALDI samples (112). From these mass spectra, the decrease or non-decrease in the indicators is derived in relation to the decrease in the medium containing no antibiotic. Decreases in the indicators in cultures containing antibiotics indicate resistance.

The methods have so far been carried out with MALDI ionization. MALDI has the great advantage that it forms almost only singly charged molecular ions. This means that the mass spectra are not overloaded despite the 100 to 300 peaks which appear in the preferred mass range from 500 to 2,000 daltons. It is possible to use any type of mass spectrometer with MALDI ion sources for this, for example time-of-flight mass spectrometers, and also ion trap mass spectrometers. Particularly advantageous are tandem mass spectrometers, which can fragment selected ions in order to achieve an unequivocal detection of the indicators. The use of isotopically labeled indicators is favorable for these mass spectrometers.

It is also possible to use other types of ionization, however. Although the spray-based methods such as ESI (electrospray ionization) or DESI (direct surface ionization of solid samples by electrospray ionization) have the disadvantage that they form very large quantities of multiply charged ions, which can overload the mass spectra, they can easily be coupled with separation methods such as liquid chromatography (HPLC) or capillary electrophoresis (CE) so that it is possible to again obtain mass spectra with a simpler structure by separating the substances.

There are, however, other ionization methods which produce almost only singly charged ions, for example chemical ionization (CI). Chemical ionization can be used in conjunction with neutral spray methods, but also with laser ablation of solid samples, and in conjunction with an OTOF-MS (time-of-flight mass spectrometer with orthogonal ion injection).

The invention claimed is:

1. A method for the mass spectrometric determination of microbial resistance to an antibiotic, the method comprising:
   pre-culturing microbes in a culture medium containing a specific concentration of the antibiotic,
   adding, after said pre-culturing step, at least one further nutrient to the culture medium; and
   determining mass spectrometrically whether the at least one further nutrient of the culture medium decreases during subsequent culturing or a chemically modified variant of the at least one further nutrient increases during subsequent culturing, whereby a decrease in the at least one further nutrient or an increase in the chemically modified variant of the at least one further nutrient indicates resistance to the antibiotic at the given concentration.

2. The method according to claim 1, wherein the decrease in the further nutrient or the increase in the chemically modified variant of the further nutrient is determined by comparing peaks of the further nutrient with peaks of at least one reference substance in a mass spectrum.

3. The method according to claim 2, wherein the at least one reference substance comprises a peptide of D-amino acids.

4. The method according to claim 2, further comprising adding the at least one reference substance in a measured quantity to the culture medium after culturing has finished and before mass spectrometry.

5. The method according to claim 1, wherein the at least one further nutrient is a peptide, and inhibitors for already secreted peptidases are added after the addition of the at least one further nutrient.

6. The method according to claim 1, wherein said further nutrient comprises at least one peptide, and wherein the decrease in the at least one peptide or the increase in chemically modified variants of the at least one peptide is determined by mass spectrometry.

7. A method for the mass spectrometric determination of resistance of microbes to an antibiotic, comprising:
   growing the microbes in a culture medium which contains a specific concentration of the antibiotic and at least one nutrient peptide containing a core peptide of D-amino acids;
   and measuring by mass spectrometry to determine whether the core peptide of D-amino acids is increased.

8. The method according to claim 1, wherein the culture medium is a synthetic culture medium.

9. The method according to claim 7, wherein the culture medium is a synthetic culture medium.

10. The method according to claim 7, wherein the increase in the core peptide of D-amino acids is determined by comparing peaks of the core peptide of D-amino acids with peaks of at least one reference substance in a mass spectrum.

* * * * *